United States Patent [19]

De Baere

[11] Patent Number: 5,318,909
[45] Date of Patent: Jun. 7, 1994

[54] DEVICE FOR THE DETERMINATION OF AEROBIC BIODEGRADABILITY

[75] Inventor: Luc A. De Baere, De Pinte, Belgium

[73] Assignee: Organic Waste Systems, naamloze vennootschap, Antwerpen, Belgium

[21] Appl. No.: 17,409

[22] Filed: Feb. 11, 1993

Related U.S. Application Data

[62] Division of Ser. No. 687,731, Apr. 19, 1991, abandoned.

[30] Foreign Application Priority Data

Feb. 1, 1991 [BE] Belgium ............................... 9100097

[51] Int. Cl.[5] ............................................. C12M 1/34
[52] U.S. Cl. ..................................... 435/291; 435/3; 435/29; 435/289; 435/313; 435/807
[58] Field of Search ............... 435/289, 291, 313, 807, 435/3, 29

[56] References Cited

U.S. PATENT DOCUMENTS

| | | | |
|---|---|---|---|
| 3,591,458 | 7/1971 | Hardy | 435/807 |
| 3,684,702 | 8/1972 | Hartman | 435/29 |
| 3,740,320 | 6/1973 | Arthur | 195/103.5 R |
| 3,948,731 | 4/1976 | Weaver | 435/807 |
| 4,062,770 | 12/1977 | Kneer | 210/12 |
| 4,314,029 | 2/1982 | Ohtake et al. | 435/291 |
| 4,650,766 | 3/1987 | Harm et al. | 435/284 |
| 4,684,468 | 8/1987 | De Baere | 210/603 |
| 5,126,238 | 6/1992 | Gebhard et al. | 435/3 |

FOREIGN PATENT DOCUMENTS

| | | |
|---|---|---|
| 0205721 | 4/1985 | European Pat. Off. . |
| 0131319 | 3/1987 | European Pat. Off. . |
| 3214798 | 4/1982 | Fed. Rep. of Germany . |
| 3438057 | 10/1984 | Fed. Rep. of Germany . |
| 517845 | 8/1974 | Japan . |
| 56-44388 | 3/1981 | Japan . |

OTHER PUBLICATIONS

Nakasaki, et al, "Change in Microbial Numbers During Thermophilic Composting Of Sewage Sludge With Reference to $CO_2$ Evolution Rate", App. And Env. Microbio., 49(1):37–41, (1985).

*Primary Examiner*—Robert J. Warden
*Assistant Examiner*—Krisanne M. Thornton
*Attorney, Agent, or Firm*—Foley & Lardner

[57] ABSTRACT

A device for determining the aerobic biodegradability in a composting installation of at least one product includes at least two reactors, a temperature device for maintaining the reactors at a temperature above the ambient temperature, a device for passing gas which contains oxygen through the reactors, a device for separately collecting outflowing gas from each of the reactors, a measuring/calculating device for determining the amount of $CO_2$ in the outflowing gas of each reactor and a calculating device for determining the aerobic biodegradability of the at least one product based on the measured/calculated amount of $CO_2$ in the outflowing gas of each reactor.

17 Claims, 2 Drawing Sheets

DEVICE FOR THE DETERMINATION OF AEROBIC BIODEGRADABILITY

This application is a division, of application Ser. No. 07/687,731, filed Apr. 19, 1991, now abandoned.

BACKGROUND

1. Field of the Invention

The invention relates to a method for the determination of the aerobic biodegradability in a composting device of at least one product.

2. Description of the Related Art

Aerobic composting has already been utilized for a considerable time for biologically transforming organic waste products into a stabilized end product, namely compost. This composting is performed by aerating the organic waste products at a controlled degree of moisture. Bacteria and fungi are going to transform the waste products into water, $CO_2$, and compost, whereby great quantities of heat are released. For household refuse the composting normally requires 8 to 20 weeks but for difficultly degradable substances the composting can require 1 to 2 years.

Because of the increasingly stringent environmental standards and the growing environmental awareness of consumers, many producers of all sorts of consumer goods, packaging materials, chemical products etc. are forced to make more environmentally friendly products. That is why it is necessary to be able to verify how these products, after use by the consumer, can be processed in the refuse chain. If the product is considerably biodegraded in a composting device, this product is biodegradable or compostable.

Several methods are known for determining biodegradability. The known methods are especially directed towards determining the biodegradability of the products in a water purification device. Such a known method is the so-called STURM-test whereby the production of $CO_2$ by bacteria is measured in a wet environment. Since the microbiota, the temperature (10 to 20 degrees Centigrade) and other factors differ considerably in the wet conditions with less than 1% dry substance of a water purification device in relation to these factors in the dry conditions with at least 30 to 40% dry substance and a temperature above 50 degrees Centigrade of a composting device, this method is not suitable for determining the degradability in a composting device. According to other known methods the product such as plastic of which the degradability has to be measured is, together with other material placed in a composting tank and after 6 to 8 weeks again removed and subjected to tests, such as the measurement of the ductility. These methods are indirect measurements and no proof is given that the product is actually microbiodegraded.

SUMMARY OF THE INVENTION

The purpose of the invention is to provide a method for the determination of the aerobic biodegradability of at least one product under almost identical conditions to those in a real composting device.

A further purpose of the invention is to provide a method whereby this determination is performed under well defined and controlled conditions so that the results can provide statistical information of the degree and speed of the degradability of the product under specific composting conditions.

It is still further the purpose of the invention to have this determination take place under conditions which are optimum and accelerated and can be entirely controlled so that the method can be applied in different laboratories and reproduceable information be obtained.

These objectives are achieved by making use of this invention according to which a well defined amount of the product is mixed with an amount of active inoculum and, if necessary, an amount of water, such that the dry substance content of the mixture is situated between 40 and 60%, through at least one quantity of this mixture, that is maintained at a constant temperature of between 30 and 75 degrees Centigrade, gas containing oxygen is passed with a known $CO_2$ content that is preferably zero, the amount of $CO_2$ coming from the mixture is accurately measured or calculated, an amount of inoculum alone is treated in just the same manner with the gas containing oxygen and also moreover the amount of $CO_2$ in the outflowing gas is measured, and finally on the basis of the amounts of $CO_2$ the amount of carbon is determined which originates from the product alone and is converted into $CO_2$ through biological activity.

The determination of the aerobic degradability is effected under the conditions of a controlled and optimum composting.

As gas containing oxygen air, preferably $CO_2$-free air, or pure oxygen can be used.

In a particular embodiment of the invention the same amount of inoculum alone is used as the amount of inoculum in the mixture and the amount of converted carbon coming from the increased production of $CO_2$ by the mixture is determined.

In a notable embodiment of the invention the gas containing oxygen is passed through a reactor with a volume of between 2 and 6 liters of the mixture product-inoculum.

In a suitable embodiment of the invention 5 to 50% product is mixed with 95 to 50% inoculum in order to form the mixture.

The carbon content of the original product is preferably determined separately.

The amount of $CO_2$ produced can be measured by dissolving in $Ba(OH)_2$ or by measuring the added and outflowing gas flow for at least a specific time and measuring the $CO_2$ content thereof.

The invention also relates to a device which is particularly suitable for the application of the method according to one of the preceding embodiments.

The invention especially relates to a device for the determination of the aerobic biodegradability in a composting device of at least one product, characterized in that it comprises at least two reactors, means for maintaining these reactors at a temperature above the ambient temperature, means for passing gas containing oxygen through the reactors, means for separately collecting the outflowing gas from each reactor and means for measuring or calculating the amount of $CO_2$ in this gas.

The device preferably comprises means for calculating the amount of carbon which is degraded starting with these amounts of $CO_2$.

BRIEF DESCRIPTION OF DRAWINGS

In order to show better the characteristics according to the present invention, some preferred embodiments of a method and device for the determination of aerobic biodegradability according to the invention are described hereafter, as examples and without any restrictive character with reference to the enclosed drawings in which.

DETAILED DESCRIPTION OF THE PREFERRED EMBODIMENTS

Figure 1:
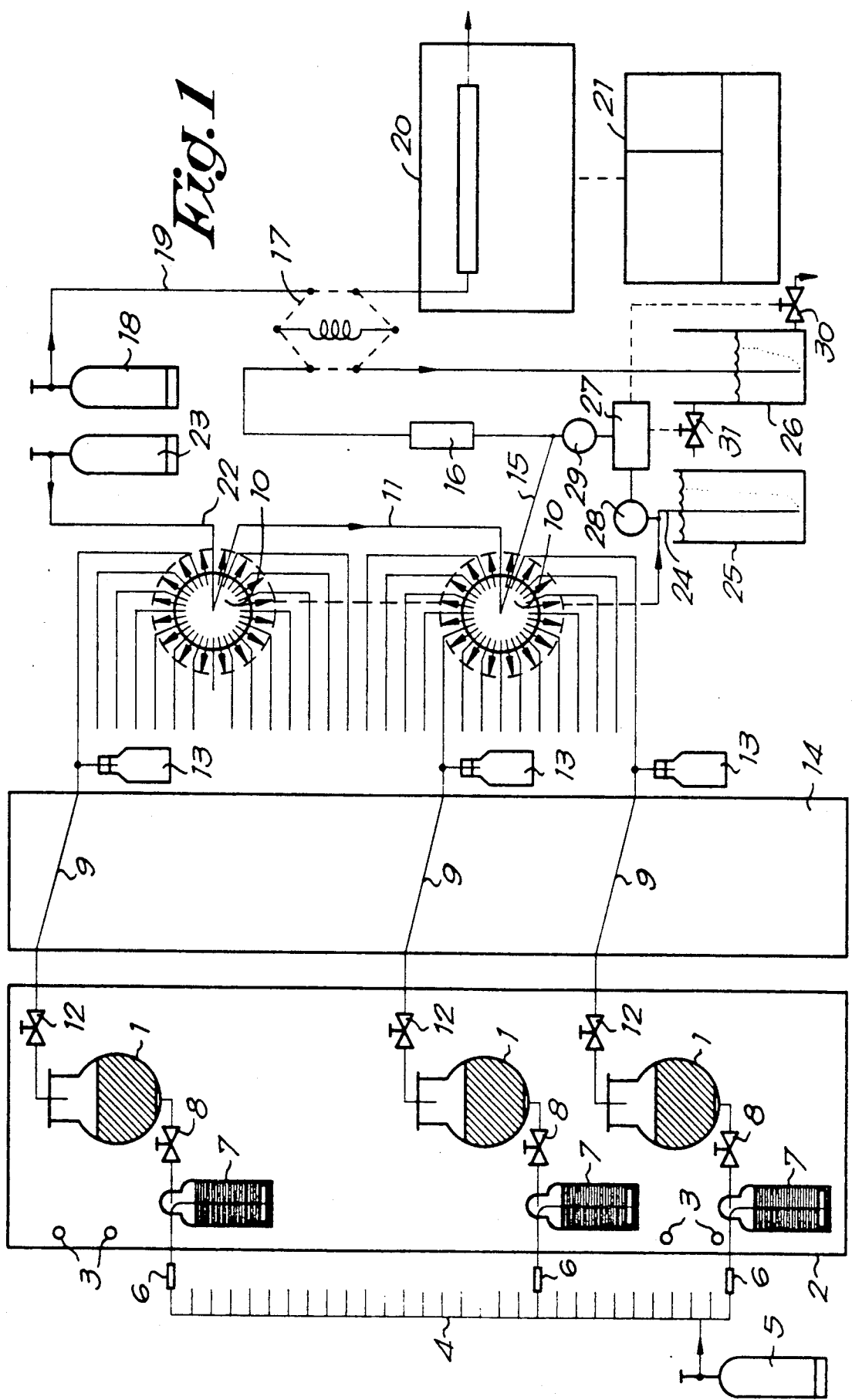
FIG. 1 shows schematically a device for the determination of the biodegradability of products according to the invention.

In order to determine simultaneously the aerobic biodegradability of a number of products, use is made of the device shown in FIG. 1.

This device comprises thirty closed reactors 1, of which for the sake of simplicity only three are drawn in FIG. 1, which are disposed in a thermally insulated incubator 2 which is maintained at a specific temperature by means of heating elements 3.

An air supply pipe 4 connects to the underside of each reactor 1. All the air supply pipes 4 are connected to the same tank 5 with dry air under pressure which is free from $CO_2$. In each air supply pipe 4 between the tank 5 and the reactor 1 is successively mounted a flow rate meter 6 with regulator, a bubbler 7 filled with water in order to reach 100% humidity and to maintain the desired dry substance content, for example of 50%, in the reactor 1, and a cut off valve 8. The bubbler 7 and the cut off valve 8 are in the incubator 2. On the upper side of each reactor 1 a gas outflow pipe 9 is connected which flows out on a multi-port valve 10. For thirty possible reactors 1 the device comprises two such valves 10 since each valve only has sixteen inlets. One outlet of one valve 10 is connected by a pipe 11 to an inlet of the other valve 10.

Inside the incubator 2 a cut off valve 12 is mounted in each gas outflow pipe 9. Outside the incubator 2 each outflow pipe 9 connects to a condensation flask 13 for the collection of the condensed water. Between the cut off valve 12 and the condensation flask 13 the gas outflow pipes 9 extend through a common cooling unit 14. The cut off valves 8 and 12 are detachable from the pipes 4 or 9 and allow both the air supply and the gas outflow to be closed and the reactor 1 to be removed from the incubator 2 in its entirety for shaking and weighing this reactor.

Every three or four hours one of the multi-port valves 10 connects a specific outflow pipe 9, possibly through the pipe 11 and the other valve 10 to a pipe 15 which connects to one outflow of a valve 10. The other outflow pipes 9 are then connected to the other outflows of the two valves 10 which themselves are connected through a pipe 24 to an open bubbler 25. In the pipe 15 which also exits on a bubbler 26 is mounted an accurate flow rate meter 16. By means of a sampling loop 17 the gas in the pipe 15 is sampled. Through this loop 17 a sample is taken along by carrier gas that is passed out of the tank 18 through the pipe 19 continually to the gas chromatograph 20 where the sample can be analyzed. The measurement results are transmitted to the data processor 21 with printer thereto connected.

From time to time, for example every three to four hours one of the valves 10 connects one outlet which connects to the pipe 15 to one inlet which itself is connected through pipe 22 to a tank 23 in which there is a gas mixture of which the composition is accurately known.

Of the products of which the aerobic degradability must be determined, first specific, preferably equal amounts are weighed out, whereby three identical amounts of each product are weighed out. Of each product the exact amount of carbon is determined according to known ways, for example according to the international standard ISO 625-1975 (F). Each of the amounts of product is subsequently mixed very thoroughly with inoculum, preferably originating from the organic fraction of household refuse, in a ratio of at least 10 to 50 weight percent product in 100% mixture. The mixture preferably comprises at least five times more inoculum than product.

The inoculum originates from the organic fraction of household refuse. This inoculum can be added fresh or an inoculum can be added that was previously composted for a certain time, namely for 2 to 4 months, preferably in the laboratory under controlled and optimum conditions. A fresh inoculum will give results which resemble more closely the real situation, while inoculum that was previously composted, will show less background production of $CO_2$ and the results will be clearer and more accurate. The inoculum preferably has such an activity that it produces between 10 and 150 mg $CO_2$ per gram volatile solid material for the first ten days and preferably has an ash content lower than 70%. The inoculum is preferably free of large inert parts such as glass, metal etc. and sieved so that the particles are smaller than 25 mm, preferably smaller than 5 mm.

If necessary the solid substance content of the various mixtures of inoculum-product is brought by the addition of water, to 40 to 60% and preferably 45 to 55% and for example 50% and these mixtures are subsequently separately placed in the reactors 1. From each product therefore three reactors have been filled with the same mixture. Three reactors 1 are however not filled with a mixture but with inoculum alone and then preferably with an amount of inoculum which is equal to the amount of inoculum in the mixtures in each of the other reactors. In order to obtain appreciable heating in the reactors 1, the volume of the mixtures in the reactors 1 is situated between two and six liters. As reference for one of the products a material can be used of which the aerobic degradability is known, such as cellulose for example. During determination with the assistance of the heating elements 3 which have been arranged in the incubator 2 as shown in FIG. 1, the temperature in the reactors 1 is maintained as constant as possible at a value between 30 and 75 degrees Centigrade and preferably at 50 degrees Centigrade. Temperature deviations are limited to 2 degrees.

For a period of 20 to 70 and preferably 45 to 60 days but possibly longer if necessary, a well defined flow of $CO_2$-free air is allowed to flow from the tank 5 through the bubbler 7 where the air is humidified, into the reactor 1 and therefore through the material installed therein. The flow that passes through the reactors 1 must be sufficiently great in order to ensure that the oxygen in the gases flowing out of the reactor is not entirely used up and that preferably the oxygen content does not descend below 6% and preferably not under 8%. This flow is established by means of the flow rate meters 6 with regulators.

In a variant pure oxygen can be added in place of air in which case the flow rate can be less.

Because of the fact that the bubblers 5, in which the added air is humidified is at the same temperature as the reactors 1 condensation in these reactors 1 is avoided. The bacteria and fungi can under optimum conditions in warm and sufficiently humid conditions bring about biodegradation in the reactors 1 and convert the carbon in the material into $CO_2$.

The gases which are removed separately from the reactors 1 through the gas outflow pipes 9 are cooled in the cooling unit 14 first down to a temperature lower than 4 degrees Centigrade. Subsequently they are sent to the multi-port 10. Of all the gas flows, of which the multi-port valves 10 successively send an amount to the flow rate meter 16, the flow is very accurately determined with this flow rate meter at regular time intervals so that from there the development of the gases flowing out of the reactors 1 can be deduced in function of time.

In order to measure accurately the flow that effectively goes through the reactors 1 and the whole device, with the transfer from one reactor 1 to another reactor 1, for the first two to three minutes, the pressure in the pipe 15 is made equal to the pressure in the common pipe 24. Use is hereby made of a pressure regulator 27 which is connected to two pressure sensors 28 and 29, respectively to the pipe 24 and the pipe 15. The overpressure by the water in the bubbler 25 is so adjusted that it is always higher than the pressure over the flow rate meter 16.

With the transfer from one reactor 1 to another reactor 1, another pressure will build up in the pipe 15 in function of among others the flow rate that is adjusted in the flow rate regulator of the flow rate meter 6 for that specific reactor 1. This pressure is observed by the pressure sensor 29 and transmitted to the pressure regulator 27 which is connected to the pressure sensor 28. If the pressure in the pressure sensor 29 becomes higher than the pressure in the pressure sensor 28, then the pressure regulator 27 will open the valve 30, through which water from the bubbler 26 flows outward and the overpressure on the pipe 15 decreases until one pressure in the pipe 15 is equal to the pressure in the pipe 24.

If, when transferring to new reactor 1 to be sampled, the pressure in the pipe 15 descends and becomes less than the pressure in the pipe 24, then the pressure regulator 27 opens the valve 31, through which water is supplied to the bubbler 26, until the two pressure sensors 28 and 29 measure the same pressure in the pipes 24 and 15.

Only when this is reached is the flow rate in the pipe 15 accurately measured by the flow rate meter 16 and signalled through to the data processor 21 as correct flow rate. After the measurement of the flow rate, after approximately 3 minutes after the transfer, for about thirty seconds the gas in the pipe 15 is sampled via the sampling loop 17 and a gas sample with carrier gas is taken out of the tank 18 through the pipe 19 to the gas chromatograph 20.

In this manner both an exact determination of the flow rate that goes through the reactor 1 and the composition of the gas that comes from the same reactor is obtained.

The amount of $CO_2$ produced is calculated on the basis of flow rate and the $CO_2$ content that is measured with the gas chromatograph 20. Of course an average is made from the three amounts of a same mixture in a group of three reactor 1. Because of the fact that three reactors 1 are filled with inoculum alone it is possible to calculate in the same manner the amount of $CO_2$ originating from the inoculum in a specific mixture. The increased production of $CO_2$ by this mixture consequently originates from the product in the mixture.

Before the amounts of gas are used for the calculation the measured or calculated volumes are reduced to volumes at standard temperature and pressure.

The percentage of biodegradability is calculated by the net amount of gaseous carbon produced by a product that is part of a specific mixture divided by the amount of solid carbon which was originally present in this same product, and multiplied by one hundred.

In a variant of the above described method the amounts of $CO_2$ produced are not calculated on the basis of flow rate measurements but by collecting and dissolving the gases originating from the reactors 1 in $Ba(OH)_2$. When this substance reacts with $CO_2$, it forms an insoluble precipitation of barium carbonate. Through titration the amount of remaining barium hydroxide can be determined: mol $CO_2$=mol $Ba(OH)_2$ at the start$-0.5$(mol HCl).

The amount of $CO_2$ produced from a product in a reactor 1 can be determined by the difference in ml of the HCl used for the titration with all gas collected from a reactor with a specific mixture and of the HCl used for the titration with all gas collected from a reactor with only inoculum multiplied by the normality of the HCl used and the molecular weight of HCl and divided by 2.

The invention will be specified in greater detail by the following concrete example.

EXAMPLE

As product of which the aerobic degradability has been determined, microcrystalline cellulose powder has been utilized for thin layer chromatography. Cellulose is generally known as a product that degrades completely but of which the biodegradation starts relatively slowly.

The organic fraction of mixed household refuse has been used as inoculum which was still after composted for eight weeks in the laboratory in order to obtain as low a background activity as possible. The dry substance of the inoculum amounted to 49.2%.

Three reactors (flasks of 4 l) have been filled with 1100 g inoculum. Three other reactors have been filled with a mixture of 1100 g inoculum and 140 g cellulose powder and 86 g water in order to obtain a solid substance content of between 40 and 60%. The six reactors have been mounted in a device as shown in FIG. 1. The heating of the incubator 2 was started and the reactors were incubated for 60 days in the dark at temperature of 50 degrees Centigrade.

Such an air flow has been passed through the reactors 1 that the oxygen content in the outflowing gases from the reactors amounted to 8%.

Figure 2:
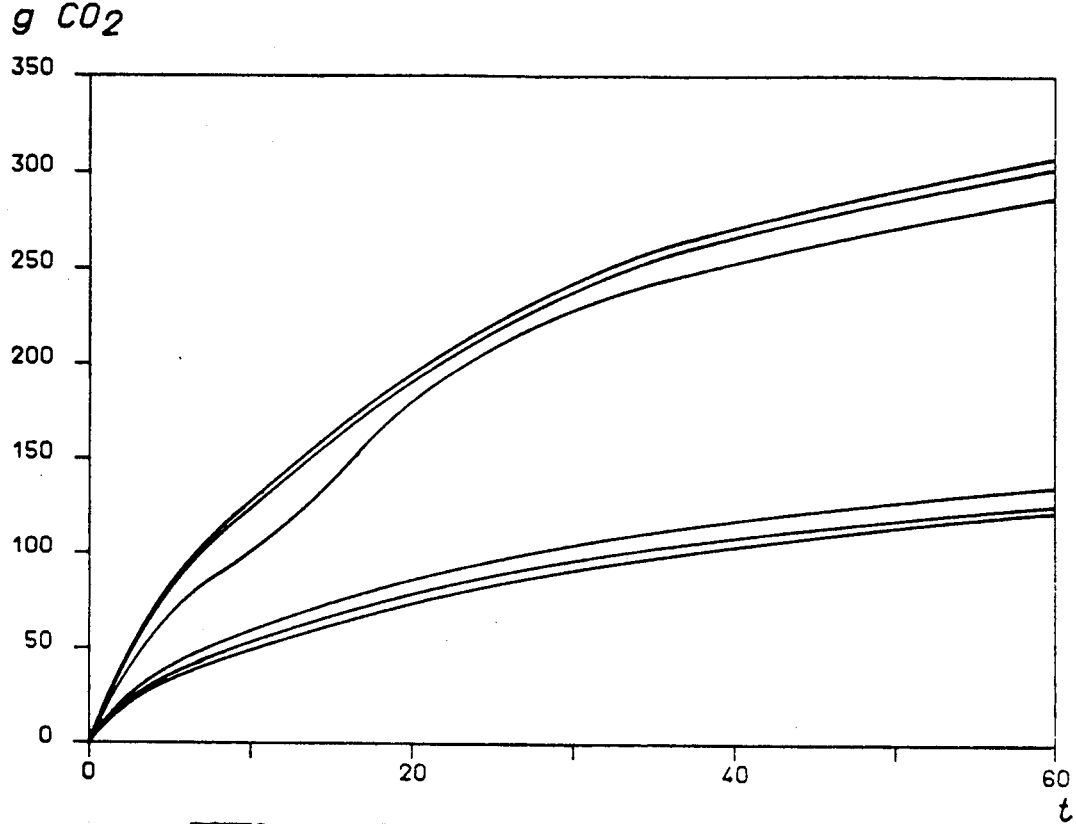
FIG. 2 shows a graph of the $CO_2$ production in function of time, during the application of the method according to the invention.
Figure 3:
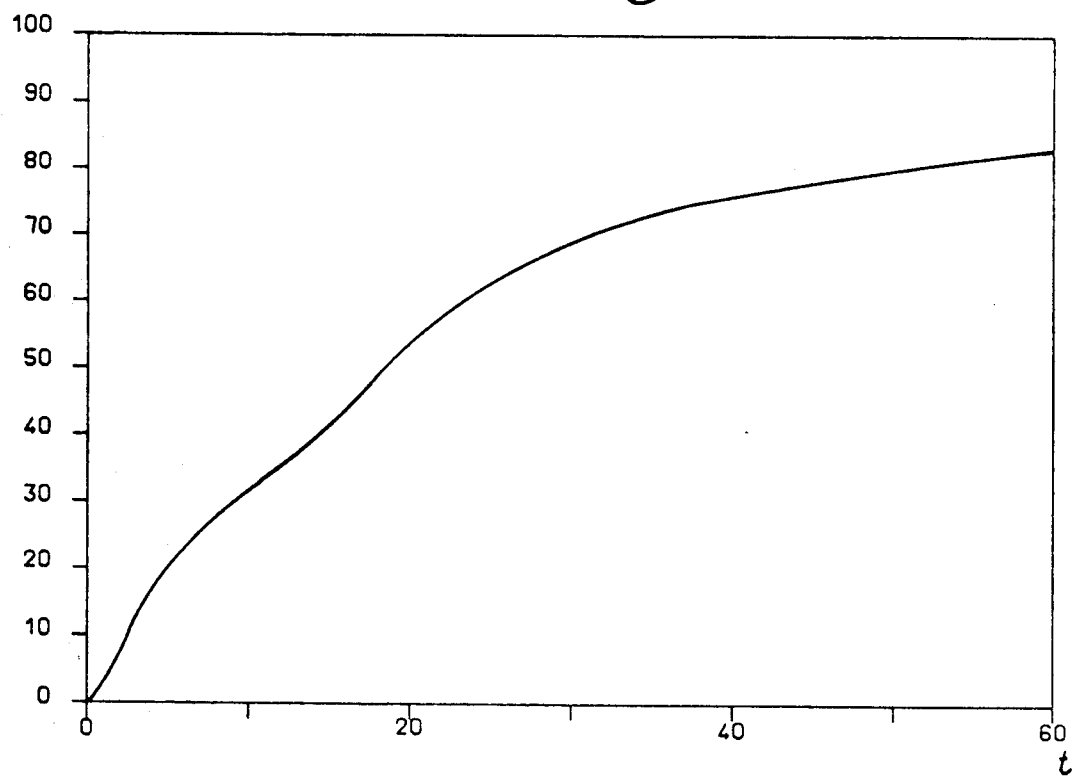
FIG. 3 shows the percentage of carbon that was converted from a product in function of time during the application of this method.

The $CO_2$ production was determined on the basis of measurements of the gas flow and the $CO_2$ concentration every three hours. The development of the cumulative $CO_2$ production in grams in function of time in days is shown in FIG. 2 respectively for the inoculum alone (the lower three lines) and for the mixture of inoculum-cellulose (the upper three lines). After sixty days the cumulative $CO_2$ production for the inoculum amounted respectively to 135.9; 125.7 and 123.4 grams and for the mixture respectively 307.6; 286.4 and 302.2 grams. After conversion the average net $CO_2$ production per unit weight of cellulose can be obtained. After sixty days this amounted to 1204 mg per gram cellulose. From this the average amount of carbon in the form of gas could be calculated while the original amount of carbon in the cellulose was also calculated with assistance of the carbon content (39.7%) of the cellulose used and the amount of cellulose in a mixture. Finally it was possible to calculate the conversion percentage of solid carbon in the cellulose into gaseous carbon in this manner. The graphic development of this percentage into % in function of time in days is shown in FIG. 3. The major part of the conversion took place in the first 30 days of the incubation. After 60 days the conversion of solid carbon originating from the cellulose into gaseous carbon amounted to 83%.

The above described method is very simple and accurate and offers reliable and reproduceable results.

The present invention is in no way restricted to the embodiments described above a i these embodiments can be implemented with many changes without departing from the scope of the present invention application.

In particular it is not necessary to treat three amounts of inoculum and three amount of mixture inoculum-product as described above. One amount is in fact sufficient, but several amounts obviously offer a greater accuracy.

I claim:

1. A device for the determination of the aerobic biodegradability in a composting installation of at least one product, the device comprising;
   at least two reactors;
   temperature means for maintaining the reactors at a temperature above the ambient temperature;
   means for passing gas which contains oxygen through the reactors;
   means for separately collecting outflowing gas from each of said reactors;
   means for measuring or calculating the amount of $CO_2$ in the outflowing gas of each of the reactors; and
   means for calculating the aerobic biodegradability of at least one product based on the measured or calculated amount of $CO_2$ in the outflowing gas of each reactor.

2. A device for the determination of the aerobic biodegradability in a composting installation of at least one product, the device comprising;
   at least two reactors;
   temperature means for maintaining the reactors at a temperature above the ambient temperature;
   means for passing gas which contains oxygen through the reactors;
   means for separately collecting outflowing gas from each of said reactors and for periodically collecting an amount of a gas mixture of known composition;
   means for delivering said gas mixture of known composition to said means for separately collecting;
   means for measuring or calculating the amount of $CO_2$ in the outflowing gas;
   means for determining a composition of said gas mixture of known composition; and
   means for calculating the aerobic biodegradability of at least one product based on the measured or calculated amount of $CO_2$ in the outflowing gas of each of the reactors.

3. The device of claim 11, further comprising at least one multi-port valve having inlets and outlets, gas outflow pipes which separately connect said reactors to respective ones of said inlets of the multi-port valve and a first common pipe connected to one of said outlets of the multi-port valve, the means for measuring or calculating the amount of $CO_2$ being connected to said first common pipe.

4. The device of claim 2, further comprising at least one multi-port valve having inlets and outlets, gas outflow pipes which separately connect said reactors to respective ones of said inlets of the multi-port valve, a gas pipe which separately connects the means for delivering a gas mixture of known composition to one of said inlets of the multi-port valve and a first common pipe connected to one of said outlets of the at least one multi-port valve, the means for measuring or calculating the amount of $CO_2$ being connected to said first common pipe.

5. The device of claim 3, further comprising a second common pipe which is connected to each of said outlets of said at least one multi-port valve which are not connected to the first common pipe and which is thus in communication with each of the at least two reactors which are not connected to the first common pipe, and means for compensating for a pressure difference between pressures existing in the first and second common pipes.

6. The device of claim 5, wherein said means for compensating for the pressure difference between the first and second common pipes includes a bubbler with which an outlet of the second pipe is in communication, a water supply pipe which is in communication with the bubbler, a first control valve in the water supply pipe, a water drainage pipe, a second control valve which connects the bubbler to the water drainage pipe, a second bubbler into which said second common pipe exits, a pressure regulator which is operably connected to the first and second control valves, and first and second pressure sensors which respectively measure the pressure in the first and second common pipes and which transmit signals representative of the respective measured pressures to the pressure regulator.

7. The device of claim 4, further comprising a second common pipe which is connected with each of said outlets of said at least one multi-port valve which are not connected to the first common pipe or to the means for delivering a gas mixture of known composition, and means for compensating for a pressure difference between pressures existing in the first and second common pipes.

8. The device of claim 7 wherein said means for compensating for the pressure difference between the first and second common pipes includes a bubbler with which an outlet of the second common pipe is in fluid communication, a water supply pipe which is in communication with the bubbler, a first control valve in the water supply pipe, a water drainage pipe, a second control valve which connects the bubbler to the water drainage pipe, a second bubbler into which said second common pipe is in fluid communication, a pressure regulator which is operably connected to the first and second control valves, and first and second pressure sensors which respectively measure the pressure in the first and second common pipes and transmit signals representative of the respective measured pressures to the pressure regulator.

9. The device of claim 1, wherein the means for measuring or calculating the amount of $CO_2$ includes a flow rate meter.

10. The device of claim 1, further comprising a sampling loop means taking samples of the outflowing gas of each of the reactors, the samples being utilized by the measuring or calculating means to calculate the amount of $CO_2$ in each of the outflowing gas of each reactor.

11. The device of claim 10, further comprising a tank for a carrier gas, a gas chromatograph and a pipe between the tank and the sampling loop and between the sampling loop and the gas chromatograph.

12. The device of claim 3, wherein said first common pipe is selectively connected to one of said outlets of said at least one multi-port valve and one of said reactors such that a test sample of outflowing gas from any one of said reactors can be selectively obtained utilizing said at least one multi-port valve and said first common pipe.

13. The device of claim 1, wherein said temperature means includes an incubator in which the reactors are mounted and controllable heating elements for heating the incubator.

14. The device of claim 1, wherein said means for collecting outflowing gas comprises outflow pipes which are connected to said reactors and a cooling unit through which said outflow pipes pass.

15. The device of claim 14, wherein condensation flasks are connected to the outflow pipes such that the outflowing gas of each of the reactors first passes by the cooling unit and then by the condensation flasks.

16. The device of claim 1, wherein said means for passing gas which contains oxygen through the reactors comprises pipes each being separately connected to one of the reactors and a bubbler mounted in each pipe.

17. A device for the determination of aerobic biodegradability in a composting installation of at least one biodegradable product which includes a known amount of solid carbon, the device comprising;

a first reactor having at least one biodegradable product and a first amount of inoculum therein;

a second reactor having a second amount of inoculum therein;

temperature means for maintaining said first and second reactors at a temperature above the ambient temperature;

means for passing gas which contains oxygen through said first and second reactors;

means for separately collecting outflowing gas from each of said first and second reactors;

means for measuring or calculating an amount of $CO_2$ in the outflowing gas of each of said first and second reactors; and means for calculating a percentage of the known amount of solid carbon which has been converted into $CO_2$ based on the measured or calculated amounts of $CO_2$ of the outflowing gas of each of said first and second reactors.

* * * * *